United States Patent [19]

Nakano et al.

[11] Patent Number: 4,943,564

[45] Date of Patent: Jul. 24, 1990

[54] INTRAARTERIAL INJECTION PHARMACEUTICALS OF 5-FLUORO-2'-DEOXYURIDINE ESTERS

[75] Inventors: Masahiro Nakano; Shoji Fukushima, both of Kumamoto; Takeo Kawaguchi; Yoshiki Suzuki, both of Tokyo, all of Japan

[73] Assignee: Teijin Limited, Osaka, Japan

[21] Appl. No.: 928,226

[22] PCT Filed: Feb. 17, 1986

[86] PCT No.: PCT/JP86/00071

§ 371 Date: Oct. 16, 1986

§ 102(e) Date: Oct. 16, 1986

[87] PCT Pub. No.: WO86/04816

PCT Pub. Date: Aug. 28, 1986

[30] Foreign Application Priority Data

Feb. 18, 1985 [JP] Japan .................................. 60-28431

[51] Int. Cl.$^5$ ............................................. A61K 31/70
[52] U.S. Cl. ......................................... 514/50; 514/51; 536/23; 536/29; 424/195.1
[58] Field of Search ............... 536/23, 29, 28; 514/29, 514/49–51

[56] References Cited

U.S. PATENT DOCUMENTS

| | | | |
|---|---|---|---|
| 3,397,268 | 8/1968 | Hunter | 514/49 |
| 4,490,336 | 12/1984 | Fujii et al. | 514/50 |
| 4,740,503 | 4/1988 | Hori et al. | 536/29 |

FOREIGN PATENT DOCUMENTS

| | | | |
|---|---|---|---|
| 0081386 | 6/1983 | European Pat. Off. | 514/51 |
| 54-122719 | 9/1979 | Japan | 514/49 |
| 58-49315 | 3/1983 | Japan | 514/50 |
| 58-124714 | 7/1983 | Japan . | |
| 60-23398 | 2/1985 | Japan . | |

OTHER PUBLICATIONS

Schwendener et al., Biochem. Biophys. Res. Commun., 126(2) 660–6 (1985),
Chemical Abstracts, 103:6653y (1985).
Schwendener et al., the Chemical Abstracts, 103:6653g (1985).
Mackles, The Chemical Abstracts, 106:55917s (1987).
Chemical Abstract, 99:218518f (1983).
Chemical Abstract, 103:215733x (1985).
Yamashita et al., Journal of Japanese Society of Angiography Interventional Radiology, vol. 3, No. 1, Mar. 1988.
Fukushima et al., Cancer Research 47, 1930–1934, Apr. 1, 1987.

*Primary Examiner*—Johnnie R. Brown
*Assistant Examiner*—James O. Wilson
*Attorney, Agent, or Firm*—Sughrue, Mion, Zinn, Macpeak & Seas

[57] ABSTRACT

Pharmaceutical preparations for intraarterial administration use comprising highly fat soluble derivatives of 5-fluoro-2'-deoxyuridine having the antitumor activity and oleaginous bases, wherein the property of selectively migrating to the tumor tissue and the accumulating function of 5-fluoro-2'-deoxyuridine esters are remarkably improved.

3 Claims, No Drawings

INTRAARTERIAL INJECTION PHARMACEUTICALS OF 5-FLUORO-2'-DEOXYURIDINE ESTERS

TECHNICAL FIELD

The present invention relates to intraarterial injection pharmaceuticals of 5-fluoro-2'-deoxyuridine esters.

More particularly, this invention relates to intraarterial injection pharmaceuticals of 5-fluoro-2'-deoxyuridine esters having a remarkably improved properties of selective migration to the tumor tissue and cumulative action comprising highly liposoluble derivatives of 5-fluoro-2'-deoxyuridine having an antitumor activity and oleaginous bases.

BACKGROUND OF THE ART

The difficulty which cancer chemotherapy encounters is that, though cancerous cells differentiate from nontumorous cells, they fundamentally arise from the same cells, and it is difficult to make the drug exercise the selective anticancer effect only on the cancerous cells. Many of the anticancer drugs now used clinically are intended to display the selective anticancer effect by utilizing the difference in the metabolic rates and turnover cycles between cancerous cells and normal cells; however, if enough anticancer effect is expected of the drug according to the dosage form and regimen conventionally adopted, the normal tissues are also affected by the toxicity of the drug too often.

For instance, it is widely known that 5-fluorouracil has a broad range of spectrum for solid tumors, but its half-life period in vivo is short when it is administered to a living body and its toxicity is found affecting the digestive system and hematopoietic system upon its administration intended for the prolonged antitumor activity continuous in time. As the method for selectively administering 5-fluorouracil to the tumor tissue, a report is made as to its hepatic artery injection for curing hepatic cancer (Chirurgia Gastroenterologica, 13, 43 (1979)). However, it is difficult to prepare 5-fluorouracil in the dosage forms of oily preparation, emulsion of oil in water type, or liposime of hold-back type for hepatic artery injection because of its low fat solubility.

On the other hand, 5-fluoro-2'-deoxyuridine, one of the metabolic products of 5-fluorouracil, is known to have the antitumor activity (Cancer Research, 18, 730 (1958)). It is said that when 5-fluoro-2'-deoxyuridine is administered to a living body, it is turned to 5-fluoro-2'-deoxyuridine-5'-monophosphate to display its activity. When administered to a living body, however, 5-fluoro-2'-deoxyuridine can not exercise its anti-tumor activity enough since its half-life period in vivo is very short (Cancer Research, 32, 1045 (1972)).

To correct such faults, various 5-fluoro-2'-deoxyuridine derivatives have been reported (Japanese Patent Laid-Open Publication Nos. 163585/'79; 49315/'83; Biochemical Pharmacology, 14, 1605 (1965)). Though these compounds have been improved in their antitumor activity, it may be said that their properties such as migratory movement to the target cancerous tissue and accumulation are far from the satisfactory improvement.

DISCLOSURE OF THE INVENTION

As the result of a strenuous study made with the object of producing a drug in the form of a preparation in which 5-fluoro-2'-deoxyuridine can be readily turned to activated 5-fluoro-2'-deoxyuridine-5'-monophosphate and can be administered continuatively to exercise the selective effect against the cancerous tissue, the present inventors have found that the object can be achieved by the intraarterial administration of a medicine prepared by dissolving a 5-fluoro-2'-deoxyuridine ester derivative in an oleaginous base, thus completing this invention.

This invention accordingly provides a medicine for intraarterial administration comprising 5-fluoro-2'-deoxyuridine ester expressed by the undermentioned formula (I), or their pharmaceutically permissible salts, and oleaginous bases

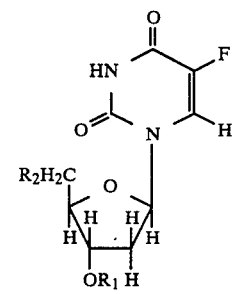

wherein $R_1$ indicates an acyl group; and $R_2$ indicates an acyloxy group or

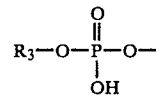

(in which $R_3$ represents a $C_5$–$C_{26}$ alkyl group).

The fat solubility of the 5-fluoro-2'-deoxyuridine esters of formula (I) is remarkably improved and accordingly its affinity for an oleaginous base is increased. Pharmaceuticals made of this 5-fluoro-2'-deoxyuridine ester and an oleaginous base, when given intraarterially, migrate selectively to the cancerous tissue and stay there. The pharmaceuticals of this invention, once taken into the cancerous tissue, remain accumulated in the cancerous tissue for a long period of time because the cancerous tissue lacks in the function of excreting foreign substances into the lymphatic system. The pharmaceuticals of this invention made to stay in the cancerous tissue continues to release 5-fluoro-2'-deoxyuridine esters, which are then hydrolyzed by esterase, which is widely distributed in the living body, into 5-fluoro-2'-deoxyuridine or 5-fluoro-2'-deoxyuridine-5'-phosphate. 5-fluoro-2'-deoxyuridine is quite readily converted into its supposed activator 5-fluoro-2'-deoxyuridine-5'-phosphate to exercise far more stronger anti-tumorous effect on the affected site than 5-fluorouracil.

In the aforementioned formula (I), $R_1$ indicates an acyl group, which includes $C_2$–$C_{22}$ aliphatic acyl groups such as acetyl, propanoyl, butyryl, hexanoyl, octanoyl, decanoyl, tetradecanoyl, hexadecanoyl, and octadecanoyl, and aromatic acyl groups such as benzoyl and toluoyl.

$R_2$ indicates an acyloxy group or

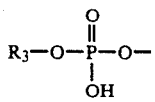

(in which $R_3$ represents a $C_5$–$C_{26}$ alkyl group). As the acyloxy group, $C_2$–$C_{22}$ aliphatic acyloxy groups such as acetoxy, propanoyloxy, butyryloxy, hexanoyloxy, octanoyloxy, decanoyloky, dodecanoyloxy, hexadecanoyloxy and octadecanoyloxy, and aromatic acyloxy groups such as benzoyloxy and toluoyloxy may be mentioned.

As the $R_3$ in

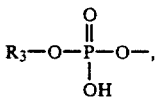

$C_5$–$C_{26}$ alkyl groups such as pentyl, hexyl, octyl, decyl, dodecyl, tridecyl, tetradecyl, pentadecyl, hexadecyl, heptadecyl, octadecyl, nonadecyl, eicosyl, docosyl, tricosyl, and tetracosyl may be mentioned.

Of all these groups mentioned above; as for $R_1$, $C_6$–$C_{18}$ aliphatic acyloxy groups such as hexanoyloxy, octanoyloxy, decanoyloxy, and dodecanoyloxy are preferable.

The 5-fluoro-2'-deoxyuridine esters of formula (I) may be their pharmaceutically permissible salts formed with such acid addition salts as hydrochloric acid, hydrobromic acid, phosphoric acid, acetic acid, and tartaric acid, and such alkali metal salts as sodium and potassium.

The 5-fluoro-2'-deoxyuridine esters of formula (I) can be obtained by making 3'-acyl-5-fluoro-2'-deoxyuridine react with monoester phosphate or aliphatic or aromatic carboxylic acid according to a commonly known method (Japanese Patent Laid-Open Publication No. 192899/'83; Biochemical Pharmacology 1965, vol. 14, pp 1605–1619).

As the concrete examples of 5-fluoro-2'-deoxyuridine esters to be used in this invention, the following may be mentioned.

(1) 3',5'-dihexanoyl-5-fluoro-2'-deoxyuridine
(2) 3',5'-dioctanoyl-5-fluoro-2'-deoxyuridine
(3) 3',5'-didecanoyl-5-fluoro-2'-deoxyuridine
(4) 3',5'-didodecanoyl-5-fluoro-2'-deoxyuridine
(5) 3',5'-ditetradecanoyl-5-fluoro-2'-deoxyuridine
(6) 3',5'-dihexadecanoyl-5-fluoro-2'-deoxyuridine
(7) 3',5'-dioctadecanoyl-5-fluoro-2'-deoxyuridine
(8) 3',5'-dibenzoyl-5-fluoro-2[-deoxyuridine
(9) 3',5'-ditoluoyl-5-fluoro-2 -deoxyuridine
(10) 3'-acetyl-5-fluoro-2'-deoxyuridine-5'-decylphosphate
(11) 3'-acetyl-5-fluoro-2'-deoxyuridine-5'-dodecylphosphate
(12) 3'-acetyl-5-fluoro-2'-deoxyuridine-5'-tetradecylphosphate
(13) 3'-acetyl-5-fluoro-2'-deoxyuridine-5'-hexadecylphosphate
(14) 3'-acetyl-5-fluoro-2'-deoxyuridine-5'-octadecylphosphate As the oleaginous bases to be used in the present invention, iodized fatty acid triglycerides such as iodized oil and strong iodized oil; iodized poppy seed fatty acid ethyl ester; or iodized fats and oils like iodized unsaturated highly fatty acids such as linoleic acid, linolenic acid, and oleic acid; vegetable oils such as soybean oil, coconuts oil, fractionated coconuts oil, sesame oil, cotton seed oil, corn oil, peanut oil, and poppy seed oil; triglycerides of fatty acid such as glyceryl triacetate, glyceryl trihexanoate, glyceryl trioctanoate, and glyceryl tridecanoate; diesters of propylene glycol such as propylene glycol dioleate, and propylene glycol distearate; aliphatic alkyl esters such as ethyl linoleate, ethyl oleate, isopropyl myristate, isopropyl palmitate, hexyl laurate, butyl stearate, oleyl oleate, decyl oleate, myristyl myristate, myristic acid, octyl dodecyl, dimethyloctane hexyldecyl; liquid fatty acids such as oleic acid any linoleic acid; alkyl esters of lactic acid such as cetyl lactate and myristyl lactate; dialkyl ester of aliphatic dicarboxylic acid such as glutamate diethyl ester, adipate diethyl ester, and adipate diisopropyl ester; alkyl esters of aromatic monocarboxylic acid such as benzoic ethyl ester and benzoic methyl ester; dialkyl esters of aromatic dicarboxylic acid such as diethyl phthalate and dibutyl phthalate; and higher alcohols such as oleic alcohol and lauryl alcohol are desirable.

Of these mentioned above, odized fats and oils such as iodized poppy seed oil aliphatic alkyl ester; vegetable oils such as soybean oil, coconuts oil, and fractionate coconuts oil; and triglyceride of fatty acid are such desirable.

Pharmaceutical preparations for intraarterial administration use of this invention can be obtained by dissolving at least one of the aforementioned 5-fluoro-2'-deoxyuridine esters in at least one of said oleaginous bases. It is a matter of course that two or more kinds of the aforementioned 5-fluoro-2'-deoxyuridine esters and two or more kinds of said oleaginous bases can be combined into a pharmaceutical preparation.

The pharmaceutical preparations of this invention are prepared by directly dissolving the aforementioned 5-fluoro-2'-deoxyuridine ester in an oleaginous base or, in case where the compound has difficulty in dissolving in an oleaginous base, a method may be adopted in which both elements are dissolved in a common solvent, dissoluble for both elements, such as ethyl acetate, ethanol, etc. separately, the obtained solutions are then thoroughly mixed, and lastly the solvent is removed from the mixture under reduced pressure.

The amount of an oleaginous base to be used for the 5-fluoro-2'40 -deoxyuridine ester can be selected from a wide range arbitrarily and its amount generally ranges from 0.1 to 1,000 times by weight as much as the 5-fluoro-2'-deoxyuridine ester.

The pharmaceutical preparation of this invention can be prescribed for intraarterial injection according to a generally known method of manufacturing technique.

Thus obtained pharmaceutical preparation of 5-fluoro-2'-deoxyuridine ester displays excellent properties of selective migration to the cancerous tissue and cumulative activity and can be used as the drug which exercises an outstanding pharmacological activity against cancer of the liver, cranial cancer, gallbladder cancer, stomach cancer, mammary cancer, lung cancer, esophagus cancer, colon cancer, renal tumors, and skin cancer.

BEST MODE OF CARRYING OUT THE INVENTION

The following examples of several most preferred embodiments will further serve to illustrate the present invention.

EXAMPLE 1

Antitumor activity of pharmaceutical preparations comprising 5-fluoro-2'-deoxyuridine esters and oleaginous bases The antitumor effect of an iodized poppy seed fatty acid ethyl ester solution of 3',5'-dioctanoyl-5-fluoro-2'-ester solution of 3',5'-dioctanoyl-5-fluoro-2'-deoxyuridine prepared according to the present invention was determined by use of rabbits bearing Vx-2 tumor.

The experiment was made by using male white rabbits which, under pentobarbital anesthesia, had their abdomens opened to have an about 1.0 mm$^3$ block of Vx-2 tumor implanted into the subcapsular parenchyma of the liver, which tumors were found growing to 1 to 3 cm in diameter upon opening the abdomens two weeks later.

An iodized poppy seed fatty acid ethyl ester solution of 3',5'-dioctanoyl-5-fluoro-2'-deoxyuridine was injected into the left proper hepatic artery of the rabbits (groups of 5 rabbits) with the use of a hepatic artery injection device consisting of a 30 gauge lymphatic duct needle, a #3 polyethylene tube, and a syringe.

The antitumor effect of the pharmaceutical preparation was examined on the group of rabbits given the preparation to see the survival days after the implantation of tumor, the result of the histological observation of tumor implanted site at the time of death or 90-day survival, and the degree of metastatis to other internal organs as compared with the group untreated and the group given an iodized poppy seed fatty acid.

The results relating to the survival days are shown in Table 1.

TABLE 1

Life prolongating effect of an iodized poppy seed fatty acid ethyl ester solution of 3', 5'-dioctanoyl-5-fluoro-2'-deoxyuridine on rabbits with Vx-2 tumor

| Treatment | Average survival days | Surviving for 90 days or more |
|---|---|---|
| Untreated | 34.0 | 0/5 |
| Iodized poppy seed fatty acid ethyl ester | 36.4 | 0/5 |
| Iodized poppy seed fatty acid ethyl ester containing 3',5'-dioctanoyl-5-fluoro-2'-deoxyuridine (30 mg) | 44.5 | 0/5 |
| Iodized poppy seed fatty acid ethyl ester containing 3',5'-dioctanoyl-5-fluoro-2'-deoxyuridine (50 mg) | 52.3 | 1/5 |

As seen from Table 1, an odized poppy seed fatty acid ethyl ester solution of 3',5'-dioctanoyl-5-fluoro-2'-deoxyuridine, which is one of the pharmaceutical preparations of this invention, prolonged the survival days of the rabbits implanted with Vx-2 tumor as compared with the group which was not treated and the group which was given in iodized poppy seed fatty acid ethyl ester.

The result of the histological observation shows that the rabbits of the untreated group and those of the group treated with an iodized poppy seed fatty acid ethyl ester were found with the remarkable growth of tumor at the site of its implantation but that the rabbits of the group given an iodized poppy seed fatty acid ethyl ester which contained 3',5'-dioctanoyl-5-fluoro-2'-deoxyuridine definitely showed no sign of tumor cells at the site of implantation.

Also no metastatis was found developing outside the implanted site with the rabbits surviving 90 days or more belonging to the group given an iodized poppy seed fatty acid ethyl ester which contained 50 mg of 3',5'-dioctanoyl-5-fluoro-2'-deoxyuridine.

EXAMPLE 2

Antitumor activity of pharmaceutical preparations comprising 5-fluoro-2'-deoxyuridine esters and oleaginous bases The antitumor effect of the pharmaceutical preparations of this invention prepared by respectively dissolving 3',5'-dioctanoyl-5-fluoro-2'-deoxyuridine, 3',5'-didecanoyl-5-fluoro-2'-deoxyuridine, and 3',5'-didodecanoyl-5-fluoro-2'-deoxyuridine in an iodized poppy seed fatty acid ethyl ester was determined by using rabbits with Vx-2 tumor.

The experiment was made by using male white rabbits anesthetized with pentabarbital which had their abdomens opened to have an about 1.0 mm$^3$ block of Vx-2 tumor implanted into the subcapsular parenchyma of the liver, which tumors were found growing to 1 to 3 cm in diameter upon opening their abdomens two weeks later.

Iodized poppy seed fatty acid ethyl ester solutions of the respective 5-fluoro-2'-deoxyuridine esters mentioned above were injected into the left proper hepatic artery of the rabbits (groups of five rabbits) with the use of a hepatic artery injection device consisting of a 30 gauge lymphatic duct needle, a #3 polyethylene tube, and a syringe.

The antitumor effect of the pharmaceutical preparations was examined by comparing the size of the tumor at the time of administering the pharmaceutical preparation (2 weeks after the implantation) with the size (growth rate) of the tumor one week after the administration of pharmaceutical preparation as compared with the group untreated and the respective groups which were given an iodized poppy seed fatty acid ethyl ester, an aqueous solution of 5-fluorouracil, and an aqueous solution of 5-fluoro-2'-deoxyuridine. The results are shown in Table 2.

TABLE 2

Growth suppressive effect of iodized poppy seed fatty acid ethyl ester solutions of 5-fluoro-2'-deoxyuridine esters against rabbit Vx-2 tumor

| Treatment | Growth* rate ± S.D. | N |
|---|---|---|
| Untreated | 636 ± 227 | 8 |
| Iodized poppy seed fatty acid ethyl ester | 428 ± 322 | 9 |
| Iodized poppy seed fatty acid ethyl ester containing 30 mg of 3', 5'-dioctanoyl-5-fluoro-2'-deoxyuridine | 27 ± 28 | 5 |
| Iodized poppy seed fatty acid ethyl ester containing 50 mg of 3', 5'-dioctanoyl-5-fluoro-2'-deoxyuridine | 11 ± 28 | 8 |
| Iodized poppy seed fatty acid ethyl ester containing 70 mg of 3', 5'-dioctanoyl-5-fluoro-2'-deoxyuridine | −3 ± 16 | 11 |

TABLE 2-continued

Growth suppressive effect of iodized poppy seed fatty acid ethyl ester solutions of 5-fluoro-2'-deoxyuridine esters against rabbit Vx-2 tumor

| Treatment | Growth* rate ± S.D. | N |
|---|---|---|
| Iodized poppy seed fatty acid ethyl ester containing 50 mg of 3',5'-didecanoyl-5-fluoro-2'-deoxyuridine | −7 ± 18 | 5 |
| Iodized poppy seed fatty acid ethyl ester containing 50 mg of 3',5'-didodecanoyl-5-fluoro-2'-deoxyuridine | 41 ± 50 | 5 |
| Aqueous solution containing 23.5 mg of 5-fluorouracil | 138 ± 91 | 8 |
| Aqueous solution containing 50 mg of 5-fluoro-2'-deoxyuridine | 420 ± 261 | 7 |

*(Tumor size one week after treatment/tumor size before treatment -1) × 100

It is apparent from Table 2 that iodized poppy seed fatty acid ethyl ester solutions of 3',5'-dioctanoyl-5-fluoro-2'-deoxyuridine, 3',5'-didecanoyl-5-fluoro-2'-deoxyuridine, and 3',5'-dedodecanoyl-5-fluoro-2'-deoxyuridine which are pharmaceutical preparations of this invention firmly suppressed the growth of Vx-2 tumor as compared with the group which was untreated, and the groups which were treated with iodized poppy seed fatty acid ethyl ester, an aqueous solution of 5fluorouracil, and an aqueous solution of 5-fluoro-2'-deoxyuridine respectively.

EXAMPLE 3

Preparation of intraarterial injection

An intraarterial injection was obtained by dissolving 3',5'-didecanoyl-5-fluoro-2'-deoxyuridine in linoleic acid by a ratio of 100 to 500 mg to 1 ml.

EXAMPLE 4

Preparation of intraarterial injection

An intraarterial injection was obtained by dissolving 3',5'-didecanoyl-5-fluoro-2'-deoxyuridine in iodized poppy seed fatty acid ethyl ester by a ratio of 100 to 500 mg to 1 ml.

Industrial Applications

When administered intraarterially, the pharmaceutical preparations comprising 5-fluoro-2'-deoxyuridine esters and oleaginous bases display remarkably excellent properties of selective migration to tumor tissues and accumulating function, therefore these pharmaceutical preparations are very useful as the therapeutic drugs for the cancer of the liver, etc.

We claim:

1. A pharmaceutical composition for intraarterial administration comprising:

(a) at least one 5-fluoro-2'-deoxyuridine ester represented by formula

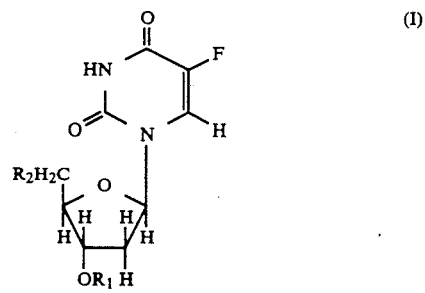

wherein $R_1$ represents a $C_8$–$C_{12}$ alkyl acyl group and $R_2$ represents a $C_8$–$C_{12}$ alkyl acyloxy group or

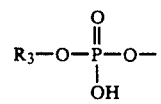

in which $R_3$ represents a $C_5$–$C_{26}$ alkyl group, or a pharmaceutically acceptable salt thereof, and (b) at least one oleaginous base.

2. A pharmaceutical composition according to claim 1, wherein said oleaginous base comprises an iodized fat or an oil.

3. A pharmaceutical composition according to claim 1, wherein said oleaginous base is a vegetable oil or a triglyceride of a fatty acid.

* * * * *